United States Patent
Glazer et al.

(10) Patent No.: US 6,232,069 B1
(45) Date of Patent: May 15, 2001

(54) RNA PROBE FOR DETECTING C-FES MRNA

(75) Inventors: Robert I Glazer, Gaithersburg; Thomas E Smithgall, Rockville; Gang Yu, Bethesda, all of MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/262,792

(22) Filed: Mar. 4, 1999

Related U.S. Application Data

(62) Division of application No. 08/252,136, filed on May 31, 1994, now Pat. No. 5,879,882, which is a continuation of application No. 07/954,427, filed on Sep. 30, 1992, now abandoned, which is a continuation of application No. 07/355,207, filed on May 22, 1989, now abandoned.

(51) Int. Cl.[7] .............................. C12Q 1/68; C07H 21/02; C07H 21/04; C12N 15/00

(52) U.S. Cl. .......................... 435/6; 536/23.1; 536/24.3; 935/76; 935/77; 935/78

(58) Field of Search ................................ 435/6; 536/23.1, 536/24.3, 24.32; 935/76, 77, 78

(56) References Cited

U.S. PATENT DOCUMENTS 4,766,072  8/1988  Jendrisak et al. .
5,968,825  * 10/1999  Ferrari et al. .................... 435/375

OTHER PUBLICATIONS

Feldman et al., Oncogene Research 1(4) : 441–458 (Sep.–Oct.' 1987).*

Matthews et al., Analytical Strategies for the Use of DNA Probes. Analytical Biochemistry 169 : 1–25 (1988).*

The Stragene Catalog p. 39 (1988).*

Avers, *Molecular Cell Biology*, Addison–Wesley Publishing Company (1986).

Promega Catalog and Applications Guide, p. 8 and 18 (1988).

Roebroek et al., The EMBO Journal 4(11)2897–2903 (1985).

Melton et al., Nucleic Acids Research, 12(18):7035–7056 (1994).

DeBold et al., Endocrinology 66(6):2648–2657 (1988).

Watson et al., Molecular Biology of the Gene, Benjmain/ Cummings Publishing Co., Inc. (1987).

* cited by examiner

*Primary Examiner*—Ethan Whisenant
(74) *Attorney, Agent, or Firm*—Fish & Richardson P.C.

(57) ABSTRACT

A recombinant plasmid and an RNA sequence expressed by said plasmid are described. The RNA sequence hybridize specifically with human c-fes mRNA.

7 Claims, 11 Drawing Sheets

RNA PROBE FOR DETECTING C-FES MRNA

This is a divisional of U.S. application Ser. No. 08/252,136, filed May 31, 1994, issued Mar. 9, 1999 as U.S. Pat. No. 5,879,882, which is a continuation of U.S. application Ser. No. 07/954,427, filed Sep. 30, 1992, now abandoned, which is a continuation of U.S. application Ser. No. 07/355,207, filed May 22, 1989, now abandoned.

The present invention is related generally to diagnostic tests. More particularly, the present invention is related to an RNA probe for detecting the presence of c-fes mRNA in biological samples, such as human cell and tissue RNA preparations.

Expression of the c-fes oncogene is known to play a certain functional role in myelopoiesis in hematopoietic cells (Smithgall et al, 1988, *J. Biol. Chem.* 263, 15050–15055; Greer et al, 1988, *Mol. Cell. Biol.*, 8, 578–587). However, heretofore direct evidence was lacking to prove that the expression of human c-fes gene induced myeloid differentiation in cells. Furthermore, a specific and sensitive assay to measure the level of c-fes mRNA in human cells and tissues was also heretofore not available.

SUMMARY OF THE INVENTION

It is, therefore, an object of the present invention to provide a kit for the detection of c-fes mRNA in biological samples such as human cell and tissue RNA preparations.

It is a further object of the present invention to provide an RNA probe for detecting the presence of c-fes mRNA in vitro or in situ.

It is another object of the present invention to provide a recombinant plasmid comprising exon 2 of the human c-fes genomic sequence for the expression of the transcription product of the c-fes oncogene in a suitable expression vector.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
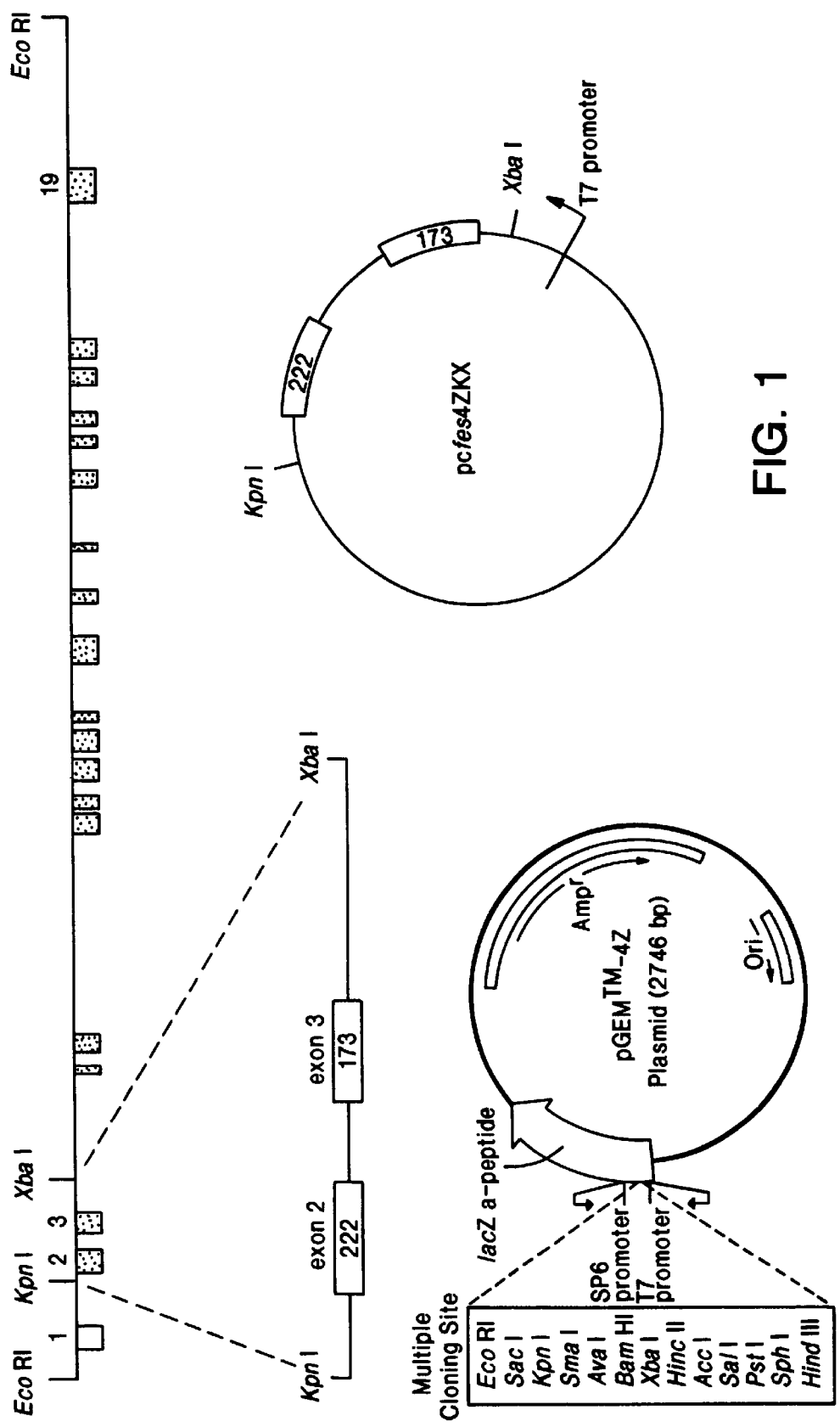
FIG. 1 shows the various elements of the human c-fes genomic clone.

The above and various other objects and advantages of the present invention are achieved by a specific RNA sequence which hybridizes only with c-fes mRNA, said specific RNA sequence being obtained from the expression of the recombinant plasmid pcfes4ZKB in a suitable expression vector, such as E. coli, yeast, viruses and other prokaryotic or eukaryotic vectors well known to one of ordinary skill in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The materials, methods and examples are illustrative only and not limiting.

Materials and Methods

Materials

All radioisotopes were obtained from Du Pont-New England Nuclear, Boston, Mass. Tyrosine-agarose, Me$_2$SO, and poly(glu,tyr)$_{4:2}$ were purchased from Sigma, St. Louis, Mo. The v-fes probe (460 bp Pst I—Pst I fragment) was purchased from Oncor, Gaithersburg, Md. Rabbit antisera to a recombinant c-fes peptide was provided by Dr. Dennis J. Slamon, UCLA School of Medicine, Los Angeles, Calif.. Geneticin (G418) was purchased from Gibco, Grand Island, N.Y. Plasmids p80 and pSV2/neo were obtained from the American Type Culture Collection, Rockville, Md. The Mac-1 monoclonal antibody against the macrophage-specific differentiation was obtained from Hybritech, San Diego, Calif. The monoclonal antibody (Ab-1) directed against the fes transforming protein common to both the Snyder-Theilen and Gardner strains of feline sarcoma virus was purchased from Oncogene Sciences, Manhasset, N.Y.

Cell Culture

HL-60, K562, and Cos-1 cells were obtained from the American Type Culture Collection. HL-60 and K562 cells were grown in RPMI-1640 medium supplemented with 10% heat-inactivated fetal calf serum, 40 mM Hepes, pH 7.4, 1 mM sodium pyruvate, nonessential amino acids, 100 units/ml penicillin, and 100 µg/ml streptomycin. Cos-1 cells were grown in Dulbecco's Modified Eagle's medium supplemented as above. All cells were subcultured twice weekly, and maintained at a density of $10^5$–$10^6$ cells/ml. HL-60 cells were treated with 1.6% Me$_2$SO for 4 days to induce granulocytic differentiation.

Preparation of Cell Extracts

Cells (0.5–1.0×$10^8$) were collected by centrifugation and washed twice in Hank's balanced salt solution containing 20 mM EDTA without Mg$^{2+}$ or Ca$^{2+}$. The cell pellet was sonicated for 5 seconds in 0.5 ml of 50 mM Tris-HCl (pH 7.5) containing 2 mM EGTA, 10 mM DTT, 0.1% Triton-X 100, 1 mM PMSF, 50 µg/ml aprotinin, 200 µg/ml leupeptin and 400 µg/ml soybean trypsin inhibitor, and centrifuged at 15,000×g at 4° C. for 10 min. The supernatant was removed and the pellet was re-extracted with an identical buffer containing 1% Triton X-100. Protein concentrations were determined using a Coomassie blue-based reagent (Pierce Chemical Co.) and BSA as a standard.

Non-denaturing Gel Assay for Tyrosine Kinase Activity

Tyrosine kinase activity present in crude cell extracts and column fractions was assayed by non-denaturing polyacrylamide gel electrophoresis as described by Glazer et al (1987) Anal. Biochem. 164, 214–220. Briefly, protein samples were subjected to electrophoresis in 4.5% polyacrylamide mini-gels (Hoefer Scientific) at 4° C. Following electrophoresis, the gels were incubated with Mg$^{2+}$, Mn$^{2+}$ and [τ-$^{32}$P]ATP in the presence and absence of poly(glu,tyr)$_{4:1}$, a synthetic polymer substrate in which tyrosine acts as sole phosphate acceptor. Following incubation at 37° C. for 30 min, the gels were washed extensively in 5% trichloroacetic acid containing 10 mn sodium pyrophosphate, dried and kinase activity was quantitated by autoradiography.

Tyrosine-agarose Chromatography, Immunoblotting, and Immunoprecipitation

One percent Triton X-100 extracts were further fractionated by tyrosine-agarose chromatography (Yu et al, 1987, J. Biol. Chem. 262, 17543–17548). Extracts were applied to 1.5 ml tyrosine-agarose columns and aliquots (10 µg of protein) present in the eluate were resolved on 7.5% SDS-polyacrylamide mini-gels using them Laemmli buffer system (Laemmli, U. K., 1970, Nature 227, 680–685). Proteins were transferred to nitrocellulose membranes using the Genie electrophoretic blotter (Idea Scientific). Immunoreactive p93$^{c-fes}$ was visualized using antiserum to a recombinant human c-fes peptide, and the Protoblot detection system (Promega Biotec) as described by the manufacturer. For immunoprecipitation, 5×$10^7$ cells were labeled by incubation at 37° C. for 18 h in 3 ml of methionine-free Iscove's Modified Dulbecco's Medium containing 5% fetal calf serum and 200 µCi/ml [$^{35}$S]-methionine (1,140 Ci/mmol). Cells were then washed, lysed and subjected to immunoprecipitation with biotlnylated anti-v-fes monoclonal antibody (Veronese et al, 1982, J. Virol. 43, 896–904) and streptavidin-agarose according to the manufacturer's protocol. Following extensive washing, immune complexes resolved by electrophoresis through 800 SDS-polyacrylamide gels. Gels were treated with Fluoro-Hance (Research Products International, Mount Prospect, Ill.) prior to autoradiography at –80° C.

Construction of the expression vector pECE/fes

An SV40-based mammalian expression vector pECE (Ellis et al, 1986, Cell 45, 721–732) was provided by Dr. William J. Rutter, University of California, San Francisco. pECE was digested with Eco RI and dephosphorylated with calf intestine alkaline phosphatase. The entire human c-fes genomic sequence was isolated as a 13.2 kb Eco RI fragment from the plasmid vector p80 (Trus et al, 1982, J. Biol. Chem. 257, 2730–2733) and cloned into the expression vector pECE. The orientation of c-fes was determined by Southern blots using the v-fes probe and it was found to be in the correct orientation such that transcription of the c-fes coding sequence is directed from the SV40 early promoter. This recombinant plasmid is designated pECE/fes.

Transfection of Cos-1 and K562 cells

Cos-1 cells (5×$10^5$ cells/100 mm plate) were transfected with 20 µg of pECE/fes by the modified calcium phosphate precipitation procedure described by Chen and Okayama (1987) Mol. Cell. Biol. 7, 2745–2752. For transient expression, analysis was performed 48 h posttransfection. K562 cells were transfected by the protoplast fusion technique (Yoakum, G. H., 1984, BioTechnicues 2, 24–31). Briefly, 100 ml of an overnight culture of E. coli transformed with pECE/fes and pSV2/neo were centrifuged at 4000×g for 15 min. The bacteria were incubated for 2 hr at room temperature (22°–24° C.) with 3 ml of a freshly prepared lysozyme solution (10 mg/ml in 20 mM Hepes, 20% sucrose, pH 7.1). The incubation was stopped by adding 0.8 ml of 1.25 M $CaCl_2$ and the protoplast preparation was diluted to 10 ml with RPMI-1640. K562 cells ($5\times10^6$ cells) were collected by centrifugation and treated for 1.5 min with 2 ml of the protoplast preparation and 1 ml of fresh 48% polyethylene glycol (mol wt 1000). The cells were then washed five times with RPMI-1640 medium in a $CO_2$ incubator with the medium changed daily for the first two days. After 48 hr, cells were split and plated at $10^3$ cells per 100 mm plate containing RPMI-1640 medium supplemented with 20% heat-inactivated fetal calf serum and 0.4% agarose (SeaPlaque, FMC) and 2.5 mg/ml G418 (Gibco) for selection. After about 14 days of incubation, colonies were selected and cultured in RPMI-1640 medium with 0.2 mg/ml G418.

Southern Blot

High molecular weight DNA, prepared by the Gross-Bellard method (Gross-Bellard et al, 1972, *Eur. J. Biochem.* 36, 32–39) was digested with either Eco RI or Xho I, separated in 0.8% agarose gels and transferred to nitrocellulose (Southern, E. M., 1975, *J. Mo. P. Genet.* 1, 327–341). Hybridization was carried out with the v-fes probe labeled with [$\alpha$-$^{32}$P]dCTP by the random primer procedure (BRL) at 36° C. for 16 hr in 50% formamide, 5×SSC, 0.50% SDS, 5×Denhardt's solution and 100 μg/ml denatured salmon sperm DNA. Blots were washed with 0.1×SSC, 0.1% SDS at 65° C.

Cloning of genomic c-fes fragments for riboprobe synthesis

A 461 bp Kpn I-Bgl II fragment of the human c-fes locus (Roebroek et al, 1985, *EMBO. J.* 4, 2897–2903) containing exon 2 and some 3' and 5' intron sequences, was cloned into the polylinker region of pGEM-4Z (Promega Biotec). This vector contains the bacteriophage T7 promoter immediately downstream from and in an opposite orientation to the cloning site, allowing for preparation of a c-fes riboprobe (antisense RNA transcript). This was accomplished by linearization of the vector 5' to the c-fes insert and incubation with T7 RNA polymerase, [$\alpha$-$^{32}$P]CTP and unlabeled nucleoside triphosphates according to the manufacturer's protocol. The resulting riboprobe is 498 nucleotides in length, as it contains some sequences transcribed from the vector template.

Poly-A$^+$ RNA Isolation and RNase Protection Assay

Total cellular RNA was prepared by guanidinium isothiocyanate extraction of $10^8$ cells followed by centrifugation through cesium chloride (Chirgwin et al, 1979, *Biochemistry* 18, 5294–5298; Glisin et al, 1973, *Biochemistry* 13, 2633–2641). Poly-A$^+$ RNA was selected from 250 μg total RNA by batch adsorption to oligo-dT cellulose (New England Biolabs). The fraction eluting from oligo-dT cellulose selection was hybridized with $10^6$ cpm of the $^{32}$P-labeled c-fes riboprobe (see above). Following overnight (about 12–16 hrs) incubation, the hybridization reaction was digested with RNase, and the protected dsRNA fragments were resolved by polyacrylamide-urea gel electrophoresis and visualized by autoradiography.

Histochemical Assays

Lysozyme activity was measured spectrophotometrically at 450 nm by the lysis of *M. lysodeikticus* (Selsted et al, 1978, *Infection and Immunity* 20, 782–791). The ability of cells to reduce NBT to formazan was assessed by the method described by Breitman et al (1980) *Proc. Natl. Acad. Sci. U.S.A.* 77, 2936–2940. Fc receptors and immunophagocytosis were determined using sheep erythrocytes coated with anti-erythrocyte antibodies (Breitman et al, 1984, in *Methods for Serum-Free Culture of Neuronal and Lymphoid Cells*. Alan R. Liss, Inc., New York, 215–236). Expression of the macrophage-specific differentiation marker, Mac-1, was examined by immunofluorescence following treatment of cells for 2 days with 100 nM TPA (Ball et al, 1982, *Proc. Natl. Acad. Sci. U.S.A.* 79, 5374–5378).

EXAMPLE

Construction of Recombinant Plasmids and Riboprobe Synthesis

Figure 2:
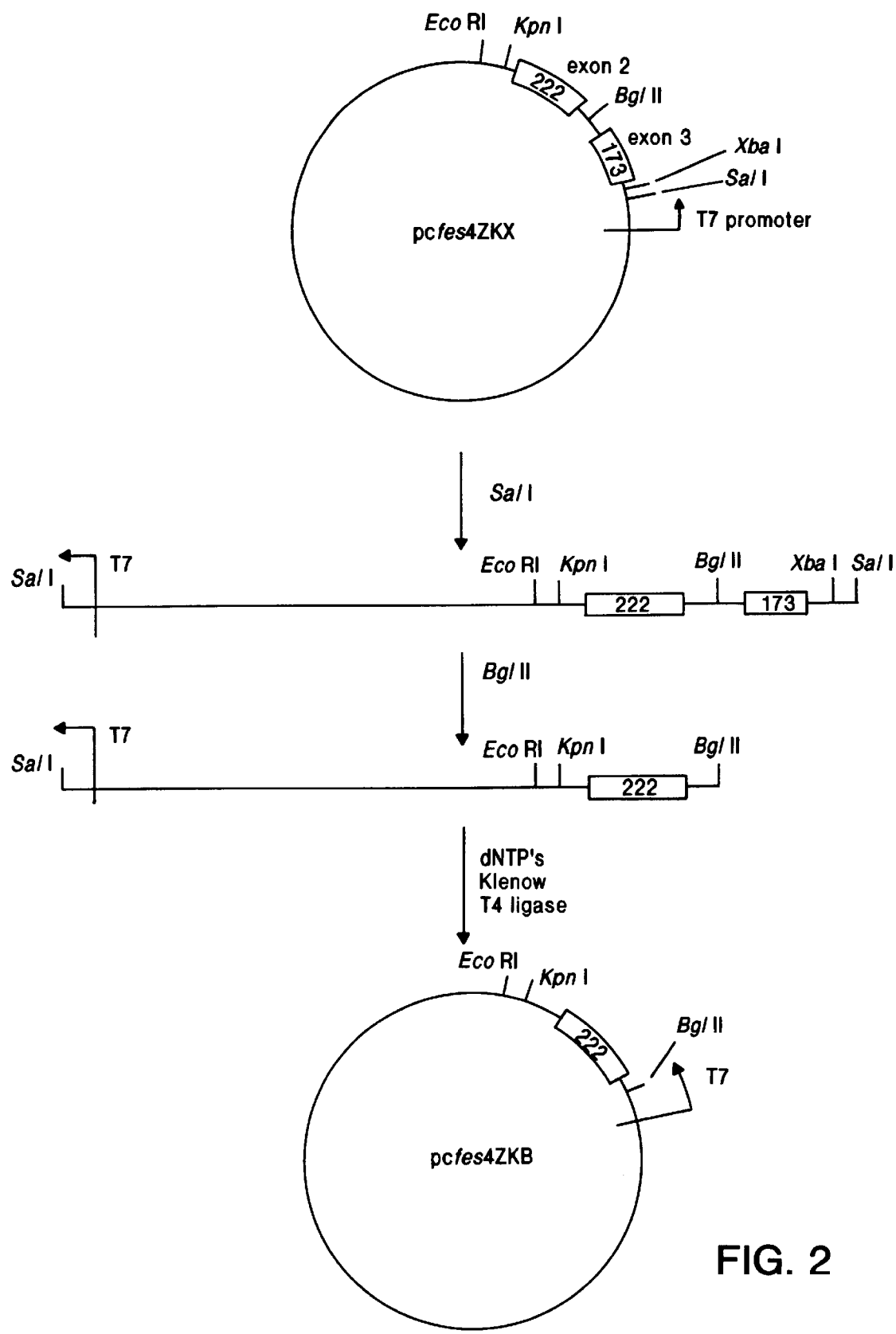
FIG. 2 shows schematic construction of the recombinant plasmid pcfes4ZKB.

The plasmid vector p80, which contains the entire human c-fes genomic sequence (Trus et al, supra), was digested with Kpn I and Xba I. The resulting 1175 bp fragment, which contains c-fes exons 2 and 3, was inserted into the polylinker region of pGEM4Z (Promega Biotec, Madison, Wis.) (FIG. 1). This recombinant plasmid, was named pcfes4ZKX. To prepare a template for riboprobe synthesis, pcfes4ZKX was digested with Bgl II and Xba I, which removed c-fes exon 3 and about two-thirds of intron 2. The terminal Bgl II and Xba I sites were filled in with the Klenow fragment of DNA polymerase, and the plasmid was re-circularized with T4 DNA ligase. The resulting recombinant plasmid, pcfes4ZKB, contains c-fes exon 2 flanked by partial sequences of introns 1 and 2 (FIG. 2). The c-fes insert is upstream from and in opposite orientation to the bacteriophage T7 promoter. Prior to riboprobe synthesis, pcfes4ZKB was digested to completion with Eco Rl, which cuts the plasmid 5' to the c-fes insert.

Figure 3:
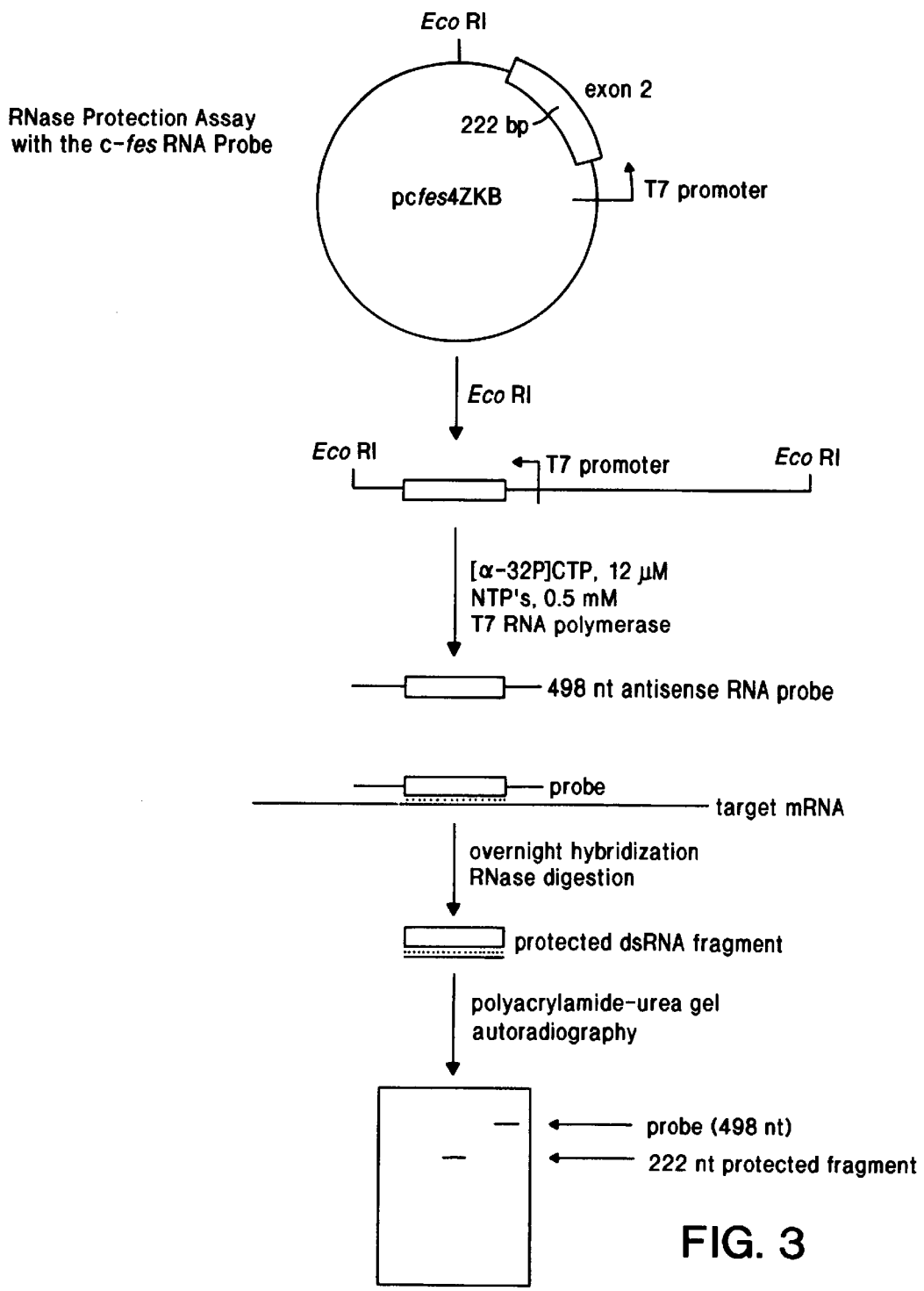
FIG. 3 schematically shows various steps involved in the RNase protection assay with the c-fes RNA probe in accordance with the present invention.

Riboprobe synthesis was conducted in a 20 μl reaction containing 40 mM Tris-HCl, pH 7.5, 6 mM $MgCl_2$, 2 mM spermidine, 10 mM NaCl, 10 mM DTT, 40 units RNasin, 0.5 mM ATP, UTP, and GTP, 12 μM CTP, 50 μCi [$\alpha$-$^{32}$P]CTP (800 Ci/mmol), and 1.0 μg linearized template DNA (FIG. 3). Reactions were initiated by adding 20 units of T7 RNA polymerase, incubated at 37° C. for 1 h, and terminated by the addition of 5 units of RQ1 DNase (Promega). Following DNase treatment for 15 min at 37° C., 2 μg of carrier tRNA were added, the reaction mixture was extracted with phenol-chloroform, and the labeled RNA was precipitated with ethanol. The riboprobe was re-dissolved in 100 μl water, and the amount of labeled CTP incorporated was determined by TCA precipitation (typically $10^6$ to $10^9$ cpm/pg RNA). The c-fes riboprobe synthesized in this manner is 498 nucleotides in length, as it contains some sequences transcribed from the parent vector. Probes were prepared on the same day they were to be used, and the best results were obtained with fresh isotope. This procedure is a modification of the method originally described by Melton et al (1984) *Nucleic Acids Res.* 12, 7035–7056.

A deposit of the recombinant plasmid pcfes4ZKB has been made at the ATCC, Rockville, Md., on May 19, 1989, under the accession number 40610. The deposit shall be viably maintained, replaced if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Results

Transfection of Cos-1 cells with pECE/fes

The 13.2 kb Eco RI fragment identified previously as the human c-fes gene (Trus et al, supra; Roebroek et al, supra) was cloned into the SV40-based mammalian expression vector pECE (Ellis et al, supra) and designated pECE/fes. To test this construct, Cos-1 cells were transfected by calcium phosphate precipitation and 48 hr later, Triton X-100 extracts of cellular proteins were analyzed for immunoreactive p93$^{c-fes}$ and for tyrosine kinase activity. Cos-1 cells transfected with pECE/fes expressed a 93 kDa protein which was specifically recognized on Western blots by the c-fes polyclonal antibody (results not shown). Extracts prepared from Cos-1 cells transfected with pECE/fes expressed a single species of tyrosine kinase activity that was present in the 1.0% Triton X-100 cell extract (results not shown). These results indicated that Cos-1 cells are capable of expressing the genomic DNA encoding c-fes and transcribing a functional gene product. However, Cos-1 cells did not acquire characteristics of myeloid cells as a result of c-fes transfection.

Co-transfection of K562 Cells with pECE/fes and pSV-2/neo

Figure 4:
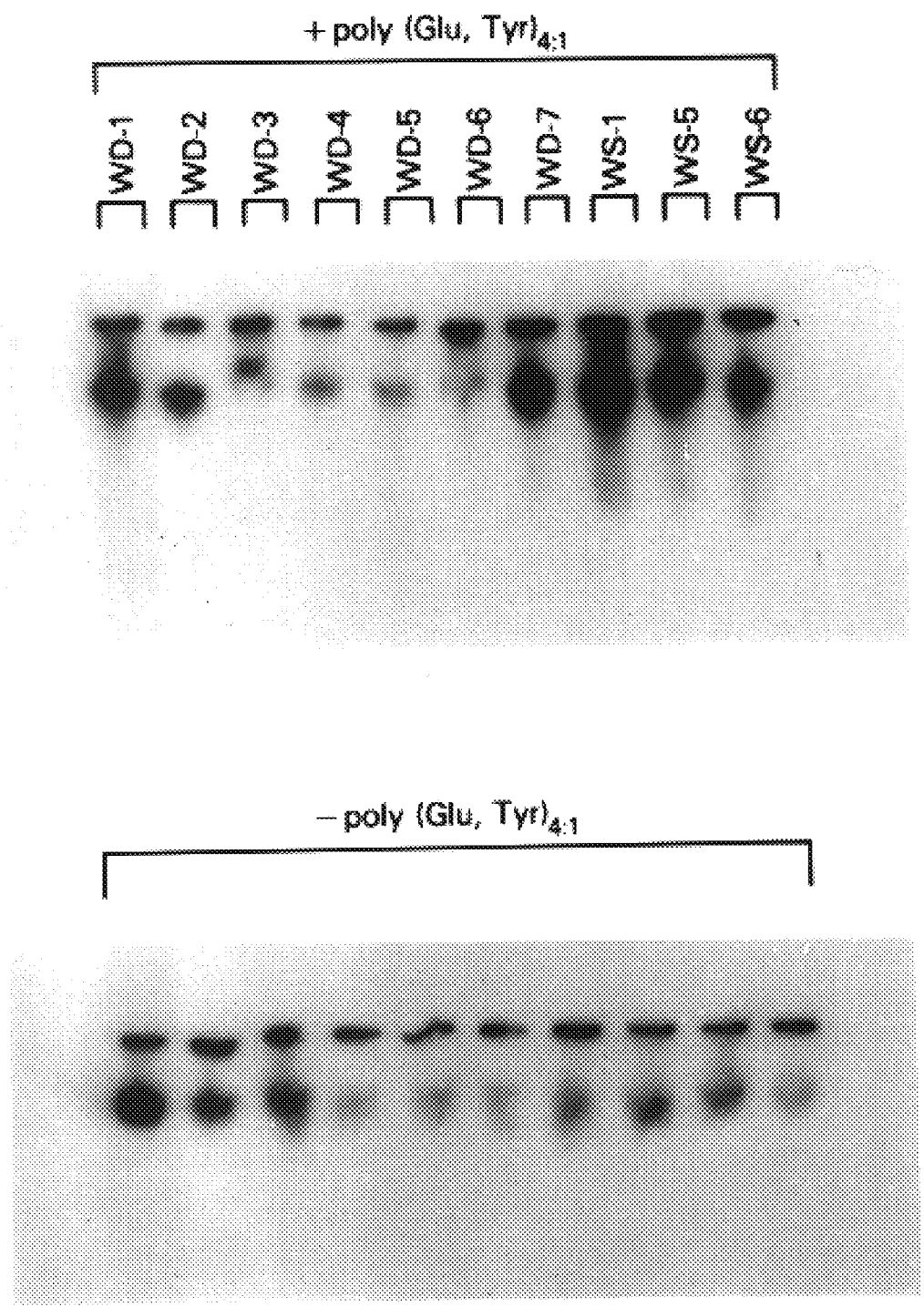
FIG. 4 shows non-denaturing gel assay for p93$^{c\text{-}fes}$ tyrosine kinase activity in colonies of K562 cells stably transfected with pECE/fes. K562 cells were cotransfected with pECE/fes and pSV2/neo as a selectable marker and G418-resistant colonies were selected and screened for p93$^{c\text{-}fes}$ tyrosine kinase activity. Aliquots of membrane proteins (15 μg) present in 1.0% Triton X-100 cell extracts were assayed for tyrosine kinase activity using the non-denaturing gel assay described in the text.
Figure 5:
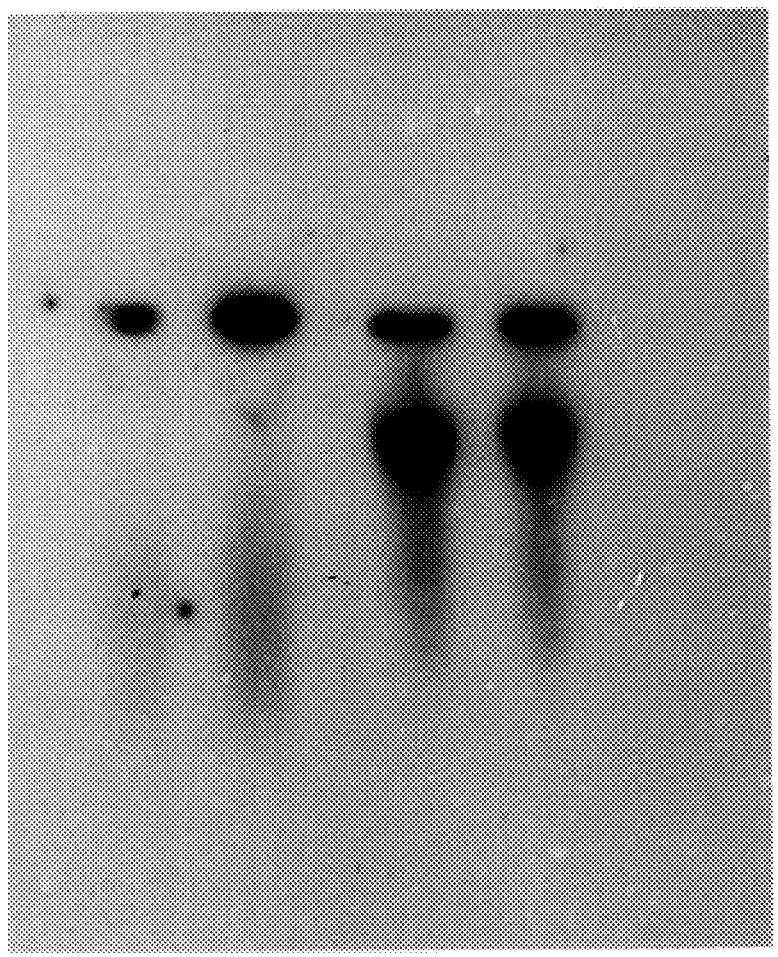
FIG. 5 shows the comparison of tyrosine kinase activity in colony WS-1 with differentiated HL-60 cells. One percent Triton X-100 extracts were prepared from either wild type K562 cells ("K562"), pSV2/neo-transfected K562 cells ("K562/neo"), colony WS-1 ("K562/fes"), or HL-60 cells treated for 4 days with 1.6% Me$_2$SO, and p93$^{c\text{-}fes}$ tyrosine kinase was partially purified by tyrosine-agarose chromatography. Eluates (3 μg of protein) were assayed for tyrosine kinase activity using the non-denaturing gel assay as described in the text.

Since K562 cells do not express p93$^{c-fes}$, they are an ideal cell line for transfection experiments with pECE/fes. K562 cells were co-transfected with pECE/fes and pSV-2/neo by protoplast fusion and were selected by cloning in soft agar containing 2.5 mg/ml G418. After 14 days in culture, G418-resistant colonies were selected and amplified in RPMI-1640 medium. One percent Triton X-100 cell extracts representing the membrane fraction of the cell were prepared from G418-resistant colonies and were screened for tyrosine kinase activity with the nondenaturing gel assay (FIG. 4). Stably transfected colonies designated WS-1, WS-5, WS-6, and WD-7 had high levels of tyrosine kinase activity. Colony WS-1 expressed a level of tyrosine kinase activity comparable to that present in HL-60 cells treated with 1.6% Me$_2$SO (FIG. 5), a treatment which produces granulocytic differentiation (Zylber-Katz et al, 1985, Cancer Res. 45, 5159–5164). p93$^{c-fes}$ tyrosine kinase activity was not present in either parental or pSV-2/neo-transfected K562 cells (FIG. 5).

Figure 6:
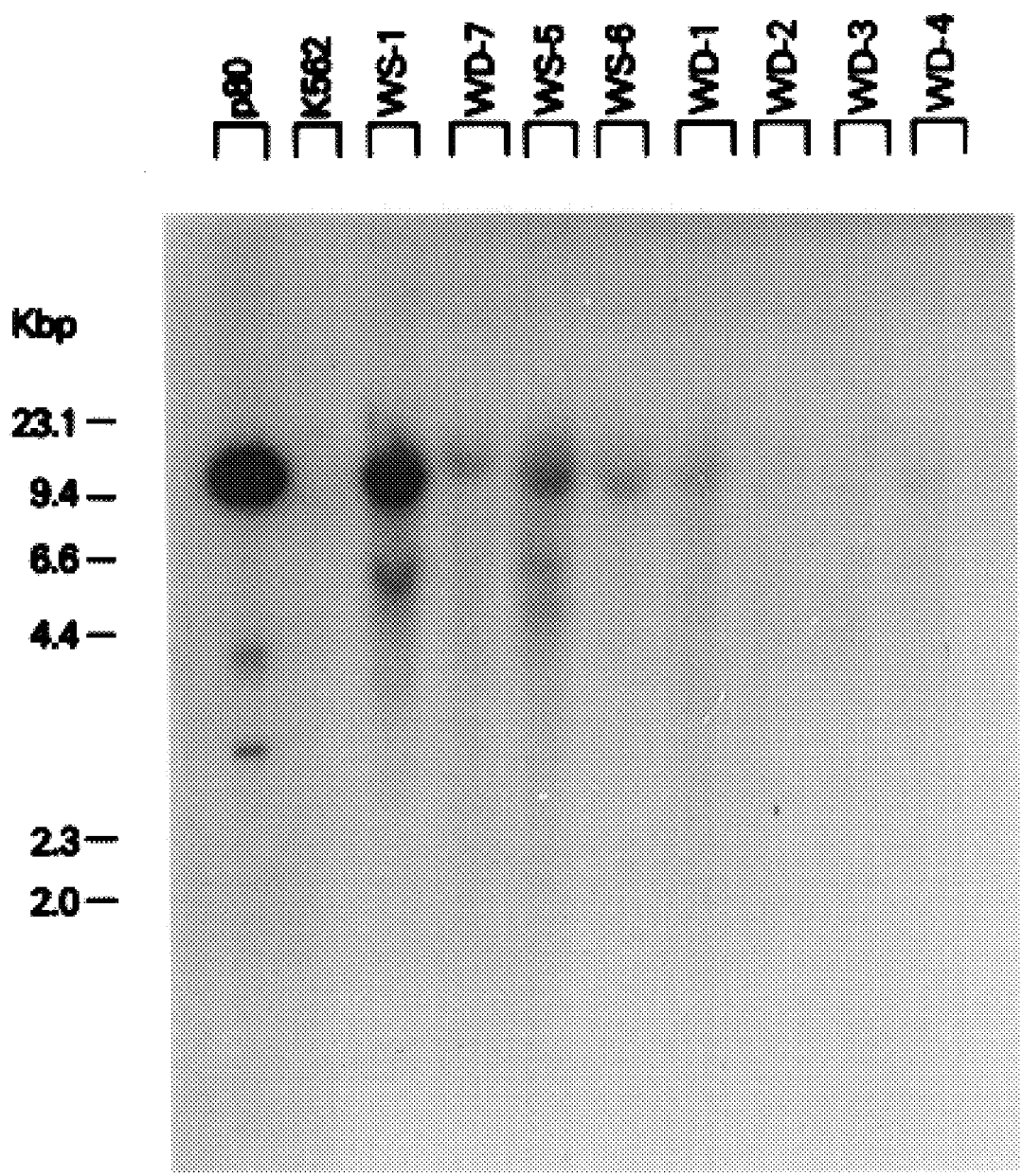
FIG. 6 shows the Southern blot analysis of colonies of K562 cells stably transfected with pECE/fes. DNA (10 μg) was prepared from wild type K562 cells ("K562") and selected colonies of cells transfected with c-fes (designated as "WS-1, WS-5, WS-6, WD-1, WD-2. WD-3, WD-4, and WD-7"), and digested with Eco RI. Plasmid p80 DNA ("p80") containing the 13.2 kb c-fes gene served as a control. After electrophoresis in 1% agarose gels, Southern blots were prepared and hybridized with a v-fes probe as described herein below. Levels of c-fes integration relative to wild type K562 cells were determined by laser densitometry of the 13.2 kb Eco RI fragment. The endogenous K562 c-fes gene is not visible in the exposure shown (12 h); determination of the c-fes gene in wild type cells required longer autoradiographic exposure (>48 h; data not shown).
Figure 7:
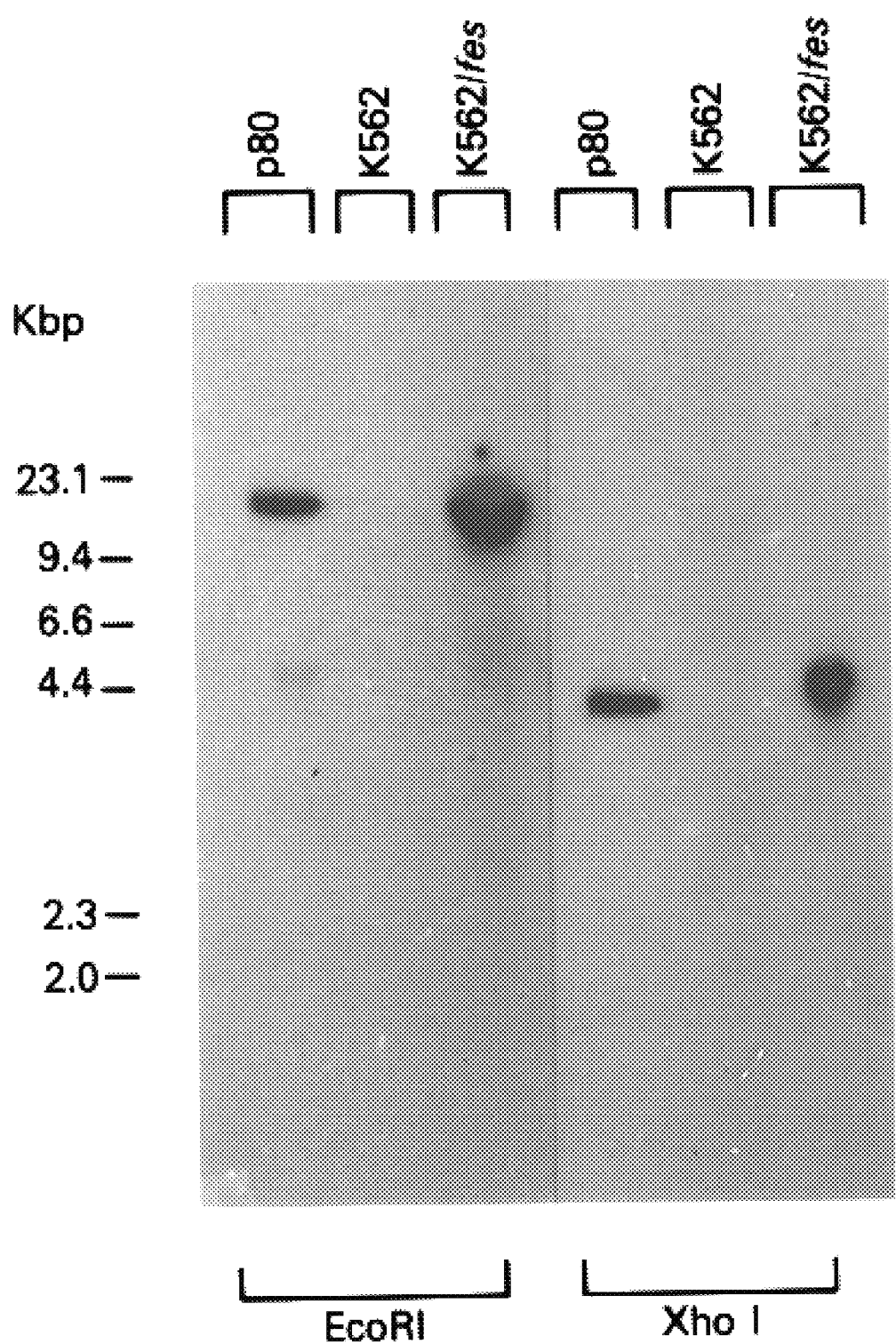
FIG. 7 shows the Southern blot analysis of a restriction digest of DNA prepared from colony WS-1. DNA (10 μg) was prepared from wild type K562 cells ("K562") and colony WS-1 ("K562/fes") and digested-with Eco RI and Xho I. Plasmid p80 DNA ("p80") containing the 13.2 kb c-fes gene served as a control. Southern blots and hybridization were carried out as described in the text.

A Southern blot of the DNA prepared from several colonies of stably transfected K562 cells indicated varying levels of integration of the c-fes gene (FIG. 6). The most dramatic example is seen in transfected clone WS-1, in which the level of the c-fes gene is more than 30 times higher than that of the K562 wild-type cells. The intensity of the hybridization signal was similar to the level of tyrosine kinase activity expressed by the various clones (FIG. 4). Digestion of WS-1 cell DNA with Eco RI and Xho I generated the expected 13.2 kb and 4.4 kb fragments that were identical to those present in p80 following hybridization with the v-fes DNA probe (FIG. 7).

Figure 8:
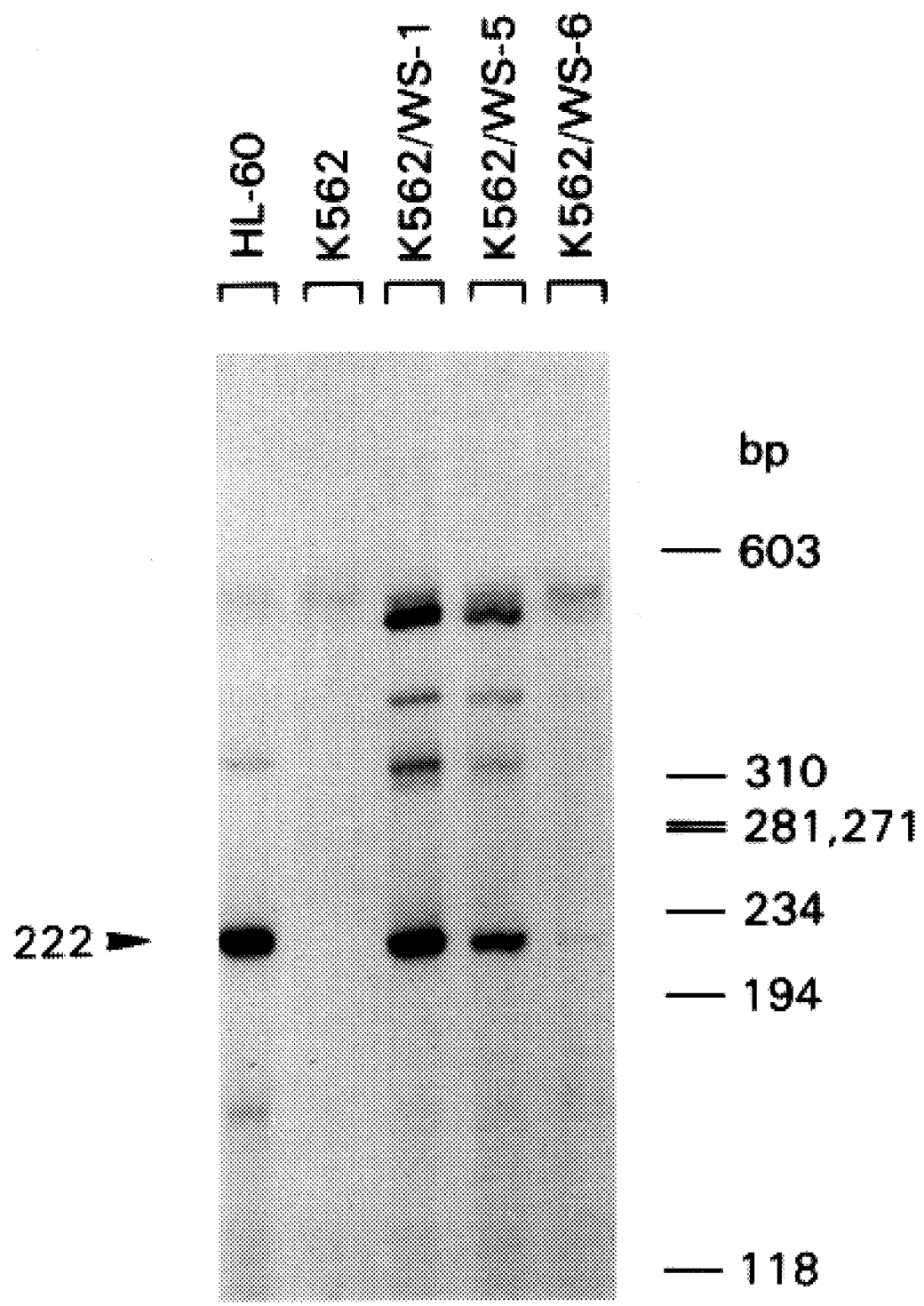
FIG. 8 shows the RNase protection assay of parental and clonal variants of K562 cells stably transfected with pECE/fes. Poly-A+ RNA was selected from 250 μg of total RNA prepared from wild type HL-60 cells ("HL-60"), wild type K562 cells ("K562"), and colonies WS-1 ("K562/WS-1"), WS-5 ("K562/WS-5") and WS-6 ("K562/WS-6"). Solution hybridization was carried out with 10$^6$ cpm of a $^{32}$P-labeled c-fes antisense RNA probe containing the 222 bp sequence complementary to exon 2 of the human c-fes gene. Following overnight incubation, the hybridization reaction was digested with RNase and the protected dsRNA fragments were resolved by electrophoresis on 6% polyacrylamide-urea gels, and visualized by autoradiography.

Analysis of c-fes transcript levels, mRNA processing, and p93$^{c-fes}$ protein synthesis in K562/fes clones Steady-state levels of c-fes mRNA were determined in transfected K562 clones using the RNase protection assay. The probe used in this assay is an anti-sense RNA transcript 498 nucleotides in length containing the 222 nucleotide sequence complimentary to c-fes exon 2. The remainder of the probe is made up of 5' and 3' sequences complimentary to c-fes introns 2 and 3, and 37 nucleotides transcribed from the vector template., Poly-A$^+$ RNA was prepared from K562/fes clones WS-1, WS-5, and WS-6 and hybridized to the c-fes riboprobe overnight. Following RNase digestion, polyacrylamide/urea gel electrophoresis revealed a major protected fragment 222 nucleotides in length in each of the transfected clones, which corresponds to c-fes exon 2 (FIG. 8). The intensity of this band is proportional to the level of c-fes genomic integration (FIG. 6), p93$^{c-fes}$ protein levels (see below). Note that an identical protected fragment is present following the RNase protection assay of poly-A$^+$ RNA from HL-60 cells, a cell line which normally expresses p93$^{c-fes}$. By contrast, no protected fragments were observed following the RNase protection assay of untransfected K562 cells.

In addition to the major band of 222 nucleotides, K562/fes clones WS-1 and WS-5 also exhibited a protected fragment of 460 nucleotides (FIG. 8), which corresponds to the size of the c-fes genomic fragment contained within the probe (i.e., intron and exon sequences). This indicates that a significant fraction of the c-fes mRNA from transfected cells contains intron sequences, and suggests that c-fes mRNA is less efficiently processed in the transfected clones than in HL-60 cells, which do not exhibit this band. Minor protected fragments approximately 320 and 370 nucleotides in length are also visible in transfected clones WS-1 and WS-5, as well as in HL-60 cells. These fragments may arise from alternate processing of the primary c-fes transcript that occurs 5' to exon 2, as several alternate splice acceptor sites have been proposed in intron 2 of the c-fes genomic sequence (Roebroek et al, supra).

Figure 9:
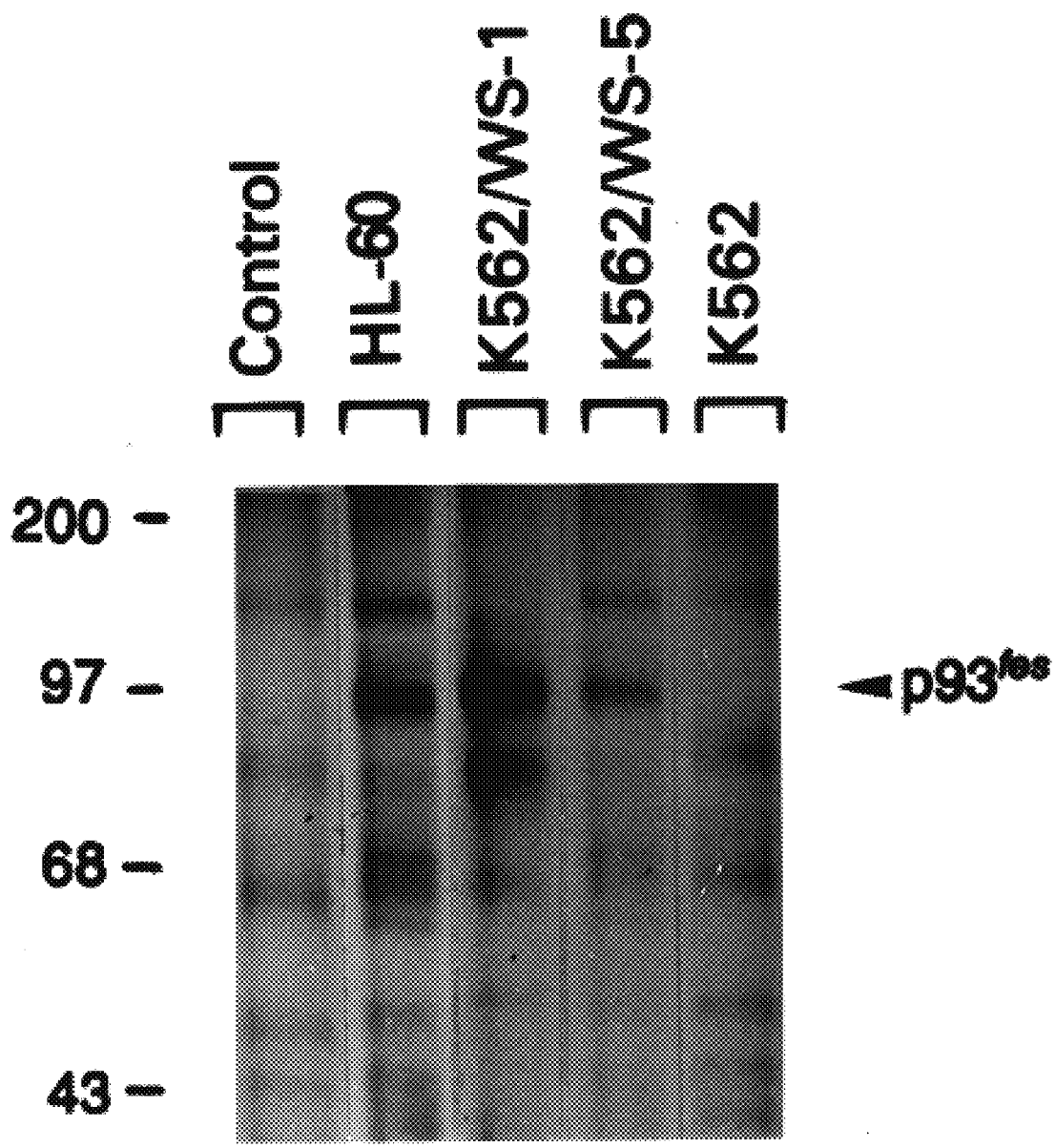
FIG. 9 shows the immunoprecipitation of parental and clonal variants of K562 cells stably transfected with pECE/fes. Cell extracts were prepared from wild-type K562 cells, transfected clones WS-1 and WS-5, and HL-60 cells labeled with [$^{35}$S]Methionine, and p93$^{c\text{-}fes}$ was immunoprecipitated with an anti-v-fes monoclonal antibody. Immunoprecipitates were analyzed by SDS-polyacrylamide gel electrophoresis and autoradiography as described in the text. The control lane shows precipitation of HL-60 extracts in the absence of the monoclonal antibody.

The results indicate that the translation of c-fes mRNA into p93$^{c-fes}$ protein proceeds normally in transfected K562 cells. This conclusion is based on immunoprecipitation experiments using an anti-v-fes monoclonal antibody. As shown in FIG. 9, transfected K562 clones WS-1 and WS-5 express an immunoreactive 93 kDa protein not seen in the K562 wild type cells. Note that an immunoreactive protein of identical electrophoretic mobility is also seen in immunoprecipitates of HL-60 cells, which are enriched in p93$^{c-fes}$.

Phenotypic alterations in colonies of K562 cells transfected with c-fes

Figure 10:
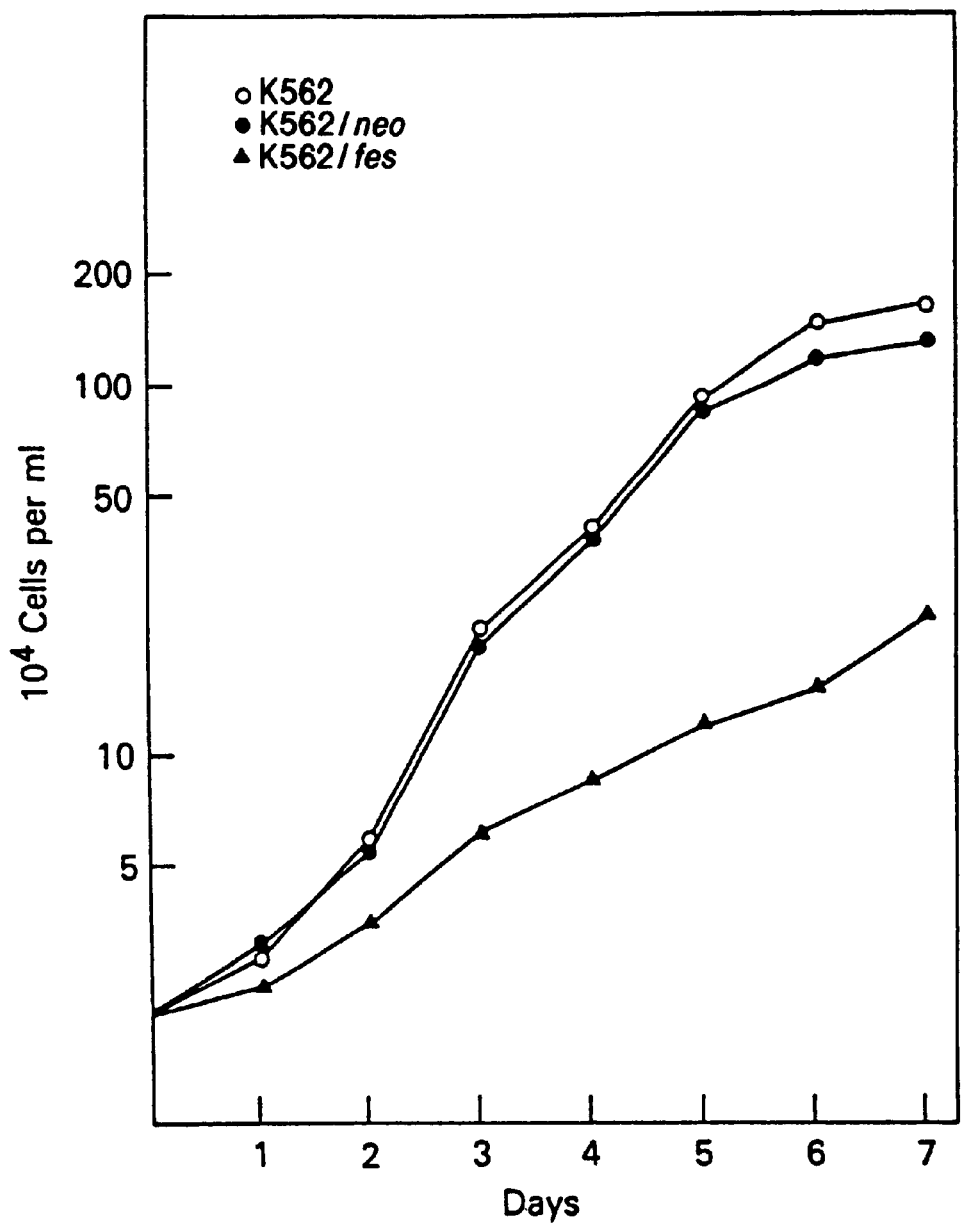
FIG. 10 shows the growth curve of K562/fes clone WS-1, K562/neo and parental K562 cells. Wild type K562 cells ("K562"), pSV2/neo-transfected cells ("K562/neo") and colony WS-1 ("K562/fes") were grown for one week, and cells number was determined at one day intervals with a Coulter particle counter. Cell viability was greater than 95% as determined by trypan blue exclusion.
Figure 11A:
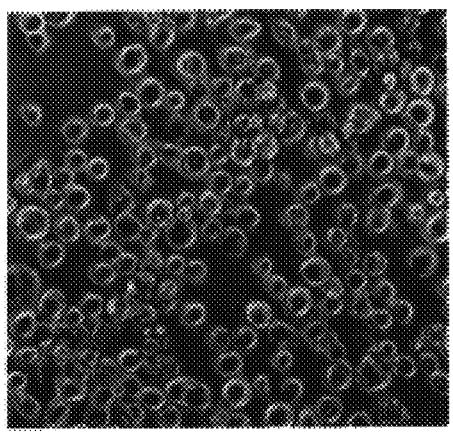
FIGS. 11A–F shows the photomicrographs of parental K562 cells and K562/fes clone WS-1. Parental K562 cells (A,C,E) and c-fes-transfected clone WS-1 (B,D,F) were tested for their response to 2 day treatment with 10$^{-7}$ M TPA (A,B), for their ability to reduce NBT (C,D) or for their capacity to phagocytize sheep erythrocytes (E,F).
Figure 11B:
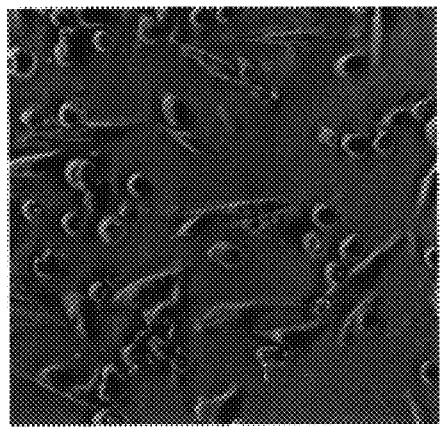
Figure 11C:
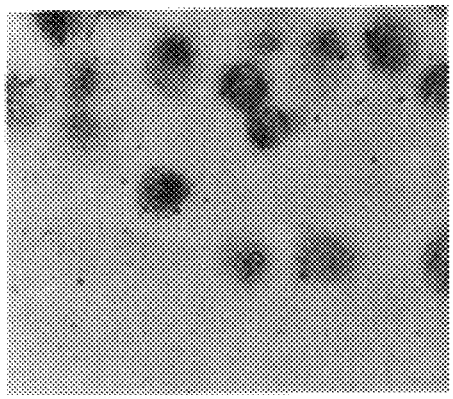
Figure 11D:
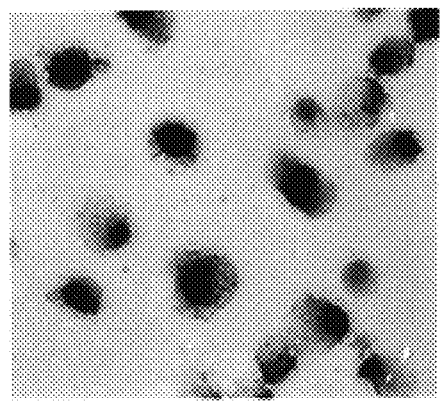
Figure 11E:
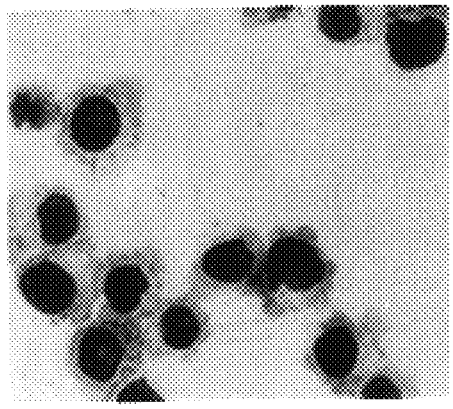
Figure 11F:
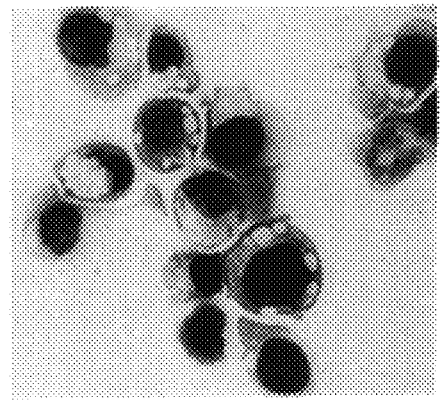

Clones WS-1, WS-5 and WS-6 were selected for further study of the changes in maturation which accompanied selection of these cell lines. After 2–3 passages, WS-1 cells grew at a slower rate than wild type K562 cells (FIG. 10), a property which may be indicative of differentiation. In addition, all clones adhered loosely to the culture flask, a property which was not seen with parental or pSV-2/neo transfected cells (Table I). Most notable was the response of WS-1 and WS-5 cells to TPA, a treatment which produced approximately 50% macrophage-like cells (FIG. 11A, B). TPA-treatment of transfected K562 cells also resulted in expression of the macrophage-specific differentiation antigen Mac-1 (Springer et al, 1979, Eur. J. Immunol. 9, 301–306), whereas TPA-treated wild type cells displayed almost no detectable Mac-1 immunofluorescence (Table I). Several functional parameters which are indicative of mature myeloid cells were also examined. Erythrophagocytosis increased dramatically in clones WS-1 and WS-5 and to a lesser extent in WS-6 (Table I and FIG. 11E, F). The percentage of Fc receptor positive cells is high in K562 cells (Koeffler et al, 1981, Cancer Res. 41, 919–926) but doubled in all the clones (Table I). Several enzymatic features of mature myeloid cells were also-acquired. In parental K562 cells, lysozyme activity was absent, but it was readily detected in all selected clones, and all transfected cell lines demonstrated high levels of NBT reduction.

Although transfected K562 cells express mature myeloid characteristics and respond to TPA, they still retain the ability to undergo erythroid differentiation in response to hemin. Treatment of K562, K562/WS-1, and K562/WS-5 with 100 mM hemin for 5 days resulted in 64%, 49O, and 63% benzidine-positive cells, respectively.

In summary, the results presented herein clearly indicate that the differentiation-associated 93 kDa tyrosine kinase activity is the product of the human c-fes gene. Expression of p93$^{c\text{-}fes}$ is found to be especially high in mature peripheral monocytes and granulocytes, acute and chronic myelogenous leukemias and in leukemia cell lines capable of myeloid differentiation such as K562 and Kg-1a, p93$^{c\text{-}fes}$ expression is either very low or absent. These findings suggest that p93$^{c\text{-}fes}$ plays a definitive role during the process of maturation of myeloid cells.

The K562 leukemia cell line provided a convenient model to study the function of the human c-fes gene and its role in myeloid differentiation. This cell line does not express p93$^{c\text{-}fes}$ and cannot be induced to differentiate along the granulocyte/monocyte pathway by a variety of differentiating agents (Koeffler et al, supra). Therefore, this cell line was utilized herein for transfection with the human c-fes gene in order to identify the role of c-fes in the differentiation process. It was observed that K562 cells transfected with the c-fes gene expressed an active p93$^{c\text{-}fes}$ tyrosine kinase which coincided with the expression of phenotypic markers indicative of a more differentiated cell type such as increased phagocytosis, Fc receptors, NBT reduction and lysozyme activity. The latter activity in clone WS-1 was comparable to levels found in mature leukocytes. This clonal cell line also responded dramatically to the phorbol ester, TPA, resulting in its morphologic transformation to a macrophage-like cell and expression of the macrophage surface antigen, Mac-1. Thus, these results demonstrate that an active c-fes gene is imperative for the ultimate expression of the mature myeloid phenotype.

For the purpose of routine assays for the detection of c-fes mRNA, non-radioactive riboprobes are easily prepared as follows.

Nonradioactive RNA probe synthesis

Two procedure can be employed to prepare nonradioactive RNA probes. The first procedure will utilize a 20 μl reaction containing 40 mM Tris-HCl, pH 7.5. 6 mM MgCl$_2$, 2 mM spermidine, 10 mM NaCl, 10 mM DTT, 40 units RNasin, 0.5 mM ATP, CTP, and GTP, 0.5 mM 5-(N-[N-biotinyl-ε-aminocaproyl]-3-aminoallyl)-uridine 5'-triphosphate, and 1.0 μg linearized template DNA. Reactions are initiated by adding 20 units of T7 RNA polymerase, incubated at 37° C. for 1 h, and terminated by the addition of 5 units of RQ1 DNase (Promega). Following DNase treatment for 15 min at 37° C., 2 μg of carrier tRNA is added, the reaction mixture is extracted with phenol/chloroform, and the labeled RNA is precipitated with ethanol.

The second method will employ the same reaction mixture except that 0.5 mM UTP is substituted for 5-(N-[N-biotinyl-ε-aminocaproyl]-3-aminoallyl)-uridine 5'-triphosphate. Following precipitation with ethanol as described above, the RNA is reacted with Photoprobe Biotin (Vector Labs, Burlingame, Calif.), a photoactivatable form of biotin which covalently labels the RNA probe.

In both instances, the biotinylated RNA probe used in the RNase protection assay is detected with a strepavidin-immunoglobulin-alkaline phosphatase conjugate utilizing NBT and BCIP for color detection (Oncor, Gaithersburg, Md.). However, other methods of color detection can, of course, also be employed as will be suggested to one of ordinary skill in the art.

A kit for the detection of c-fes mRNA comprises a container containing the riboprobe of the present invention, either prepared fresh or cryopreserved.

A method for the detection of c-fes mRNA in situ or in vitro comprises reacting a cell or tissue preparation with the radioactive or non-radioactive riboprobe of the present invention and determining the degree of hybridization by standard methodologies well known to one of ordinary skill in the art. Such methodologies include radiolabeled, immunohistochemical, fluorescence measurement and the like.

Of course, the present invention now makes it possible to induce myelopoiesis in immature myeloid cells by introducing genomic c-fes gene in immature myeloid cells in which myeloid differentiation is desired.

It is understood that the examples and embodiments described herein are for illustrative purposes only and that various modifications or changes in light thereof will be suggested to persons skilled in the art and are to be included within the spirit and purview of this application and scope of the appended claims.

TABLE I

Phenotype of parental K562 cells and colonies transfected with c-fes

| Differentiation Marker[a] | percent positive | | | | | |
|---|---|---|---|---|---|---|
| | HL-60 | K562 | K562/neo | WS-1 | WS-5 | WS-6 |
| Phagocytosis | 42[b] | 0 | 1 | 65 | 56 | 12 |
| Fc receptors | 68[b] | 52 | 48 | 94 | 85 | 81 |
| NBT reduction | 77[b] | 1 | 3 | 64 | 43 | 38 |
| Lysozyme activity[c] | n.d.[d] | 0 | 0 | 4.6 | 3.6 | 4.5 |
| Adherence | 0[b] | 0 | 0 | 80 | 80 | 65 |
| Response to 10$^{-7}$ M TPA: | | | | | | |
| Adherence | 75 | 0 | 0 | 50 | 56 | n.d. |
| Mac-1 | 88 | 2 | 3 | 70 | 73 | 18 |

[a]The values for phagocytosis, NBT reduction and lysozyme activity are the average of duplicate determinations. Other values represent a single determination.
[b]HL-60 cells were treated for 4 days with 1.25% Me$_2$SO.
[c]μg of lysozyme/10$^6$ cell. Normal leukocytes range from 3.6–8.4
[d]n.d., not determined.

What is claimed is:

1. A single stranded antisense riboprobe comprising at most about 498 nucleotides containing an RNA sequence of 222 nucleotides fully complementary to human c-fes exon-2.

2. A single stranded antisense riboprobe containing an RNA sequence of 222 nucleotides fully complementary to human c-fes exon-2 wherein said riboprobe specifically hybridizes to human nucleic acid comprising c-fes exon-2 sequences but which does not specifically hybridize to human nucleic acid lacking c-fes exon-2 sequences.

3. A kit for the detection of human c-fes RNA comprising a container containing the probe of claim 1 or 2.

4. A method for detecting the presence of human c-fes RNA in a biological sample comprising contacting the RNA present in said biological sample with the antisense riboprobe of claim 1 or 2 wherein the presence of specific hybridization between said antisense riboprobe and human c-fes exon-2 sequence indicates the presence of human c-fes RNA in said biological sample.

5. The antisense riboprobe of claim 1 or 2 wherein said antisense riboprobe is produced by transcription of a plasmid containing a DNA sequence located upstream and in opposite orientation to a bacteriophage T7 promoter.

6. The antisense riboprobe of claim 1 or 2 wherein said antisense riboprobe further comprises a detectable label.

7. The antisense riboprobe of claim 6 wherein said detectable label is selected from the group consisting of a radionuclide, biotin, a fluorescent label and an immunohistochemical agent.

* * * * *